United States Patent
Carpentier et al.

(10) Patent No.: US 7,309,748 B2
(45) Date of Patent: Dec. 18, 2007

(54) GROUP III BRIDGED IONIC METALLOCENE BASED ON CYCLOPENTADIENYL-FLUORENYL LIGANDS

(75) Inventors: Jean-Francois Carpentier, Acigne (FR); Evgueni Kirillov, Erlangen (DE); Abbas Razavi, Mons (BE)

(73) Assignee: Total Petrochemicals Research Feluy, Feluy (BE)

( * ) Notice: Subject to any disclaimer, the term of this patent is extended or adjusted under 35 U.S.C. 154(b) by 0 days.

(21) Appl. No.: 10/543,670

(22) PCT Filed: Jan. 23, 2004

(86) PCT No.: PCT/EP2004/000643

§ 371 (c)(1),
(2), (4) Date: Jun. 26, 2006

(87) PCT Pub. No.: WO2004/067591

PCT Pub. Date: Aug. 12, 2004

(65) Prior Publication Data

US 2006/0258827 A1 Nov. 16, 2006

(30) Foreign Application Priority Data

Jan. 28, 2003 (FR) .................................. 03 00918

(51) Int. Cl.
*C08F 4/6192* (2006.01)
*C08F 10/00* (2006.01)

(52) U.S. Cl. ...................... 526/164; 526/134; 526/161; 526/165; 526/319; 526/335; 526/943; 502/103; 502/152; 502/155

(58) Field of Classification Search ................ 502/103, 502/152, 155; 526/134, 161, 165, 164, 319, 526/335, 943

See application file for complete search history.

(56) References Cited

FOREIGN PATENT DOCUMENTS

JP     07 258319     10/1995

OTHER PUBLICATIONS

Evans, William J., "Activity of [Sm(C5Me5)3] in Ethylene Polymerization and Synthesis of [U(C5Me5)3), the first tris (pentamethylcyclopentadienyl) 5f-Element Complex" Angewandte Chemie, Intl Edition in English, 36(7), 774-776, 1997.

Qian, Changtao, "Cs-Symmetric ansa-Lanthanocenes Designed for Sterospecific Polymerization of Methyl Methacrylate. Synthesis and Structural Characterization of Silylene-Bridge Fluorenyl Cyclopentadienyl Lanthanide Halides, Amides, and Hydrocarbyls" Organometallics 2000, 19, pp. 4134-4140.

Barbier-Baudry, Denise et al: "Non-hindered ansasamarocenes, versatile catalysts for diene/olefin/polar monomer copolymerizations. What is really the active species?" Journal of Organometallic Chemistry, 647(1-2), 167-179, 2002.

Kirillov, Evgueni et al, "(Cp-CMe2-Flu)2Ln]-Li(ether)n]+(Ln=Y, La): Complexes with Unusual Coordination Modes of the fluorenyl Ligand and the First Examples of Bis-Ansa Lanthanidocenes" ORGANOMETALLICS, 22(20), 403824046, 2003.

*Primary Examiner*—Caixia Lu
(74) *Attorney, Agent, or Firm*—William D. Jackson; Diane L. Kilpatrick-Lee

(57) ABSTRACT

The present invention discloses a metallocene catalyst component of the formula (I) $[(\text{Flu-R''-Cp})_2\text{M}]^-[\text{Li(ether)}_4]^+$, wherein Cp is a cyclopentadienyl, substituted or unsubstituted, Flu is a fluorenyl, substituted or unsubstitutted, M is a metal Group III of the Periodic Table, and R" is a structural bridge between Cp and Flu imparting stereorigidity to the component. It further discloses a process for preparing said metallocene catalyst component and its use in controlled polymerisation.

15 Claims, 2 Drawing Sheets

GROUP III BRIDGED IONIC METALLOCENE BASED ON CYCLOPENTADIENYL-FLUORENYL LIGANDS

This invention relates to the field of metallocene catalyst systems based on a cyclopentadienyl-fluorenyl component containing a metal Group III of the Periodic Table. It also relates to controlled polymerisation based on that catalyst system.

In Razavi and Ferrara (A. Razavi, J. Ferrara, J. Organomet. Chem. 435, 299, 1992), it is shown that Group IV metallocenes of the formula $$CMe_2(Cp\text{-}Flu)MQ_2$$

wherein M is a metal Group IVB of the Periodic Table, Cp-Flu is a cyclopentadienyl-fluorenyl ligand substituted or unsubstituted, $CMe_2$ is a bridge between the cyclopentadienyl and the fluorenyl and wherein Q is hydrocarbon having from 1 to 20 atoms or a halogen, are effective precursors for stereospecific and stereoselective polymerization of propylene. Upon activation with an alumoxane these compounds produce high molecular weight syndiotactic polypropylene with very high activities.

On the other hand, some lanthanide alkyl and hydride complexes stabilised by cyclopentadienyl moieties have been known for about two decades to act as single component catalysts able to polymerise α-olefins and to initiate stereospecific polymerisation of polar monomers such as (meth)acrylates, but these are some isolated examples. They are described for example in Ballard et al. (in D. G. H. Ballard, A. Courtis, J. Holton, J. McMeeking, R. Pearce, Chem. Commun. 1978, 994.), in Watson and Parshall (in P. L. Watson, G. W. Parshall, Acc. Chem. Res. 1985, 18, 51.), in Jeske et al. (in G. Jeske, H. Lauke, H. Mauermann, P. N. Swepston, H. Schumann, T. J. Marks, J. Am. Chem. Soc. 1985, 107, 809.), in Burger et al. (in B. J. Burger, M. E. Thompson, D. W. Cotter, J. E. Bercaw, J. Am. Chem. Soc. 1990, 112, 1566.) or in Yasuda (in H. Yasuda, Prog. Polym. Sci. 2000, 25, 573.).

Dash et al. (in A. K. Dash, A. Razavi, A. Mortreux, C. W. Lehmann, J.-F. Carpentier, Organometallics, 2002, 21, 3238.) have worked on the amine elimination reactions of homoleptic amides $Ln[N(SiMe_3)_2]_3$ wherein Ln is yttrium, lanthanum or neodymium with the isopropylidene-bridged $[Cp\text{-}CMe_2\text{-}Flu]^{2-}$ ligand. The resulting complexes have been shown to be inactive in ethylene polymerization even upon activation with magnesium or aluminium alkyls.

Qian et al. (in C. Qian, W. Nie, J. Sun, J. Chem. Soc., Dalton Trans., 1999, 3283; and in C. Qian, W. Nie, J. Sun J. Organomet. Chem., 2001, 626, 171.) have shown that the salt metathesis reaction of $LnCl_3(THF)_n$ wherein Ln is Y or Lu, with the dilithiated species of the diphenyl-carbon-bridged $Cp\text{-}CPh_2\text{-}Flu$ ligand gives the structurally characterized ionic complexes $[(\eta^5,\eta^5\text{-}Cp\text{-}CPh_2\text{-}Flu)LnCl_2]^-$ $[Li(THF)_4]^+$ in good yields, but no polymerisation activity has been described.

Another publication by the same group (C. Qian, W. Nie, Y. Chen, J. Sun. In J. Organomet. Chem. 645, 82, 2002) discloses that the treatment of $[(\eta^5,\eta^5\text{-}Cp\text{-}CPh_2\text{-}Flu)LuCl_2$ $[^-]Li(THF)_4]^+$ with $LiN(SiMe_3)_2$ afforded, in a low yield of about 13%, the neutral complex $(\eta^5,\eta^5\text{-}Cp\text{-}CPh_2\text{-}Flu)LuN(SiMe_3)_2$, which was found to initiate polymerisation of caprolactone and methyl methacrylate (MMA); polymethyl methacrylate (PMMA) was produced in low activity at room temperature and contained about 60% rr dyads.

Other attempts by the same group (in C. Qian, W. Nie, Y. Chen, S. Jie, J. Organomet. Chem., 2002, 645, 82; and in W. Nie, C. Qian, Y. Chen, S. Jie, J. Organomet. Chem., 2002, 647, 114.) to extend this chemistry to "light" lanthanide metals such as for example La or Nd have failed; the successful syntheses of some derivatives $[(Cp\text{-}CPh_2\text{-}Flu)Ln((\mu\text{-}H)_3BH)_2]^-[Li(THF)_4]^+$ wherein Ln is La or Nd, also structurally characterised, stem from steric stabilisation of the system by versatile bridging bonding of tridentate $BH_4^-$ anions with the lanthanide atom.

JP-A-07258319 discloses the preparation of the neutral carbyl complex $\{\eta^5,\eta^5\text{-}Cp\text{-}CMe_2\text{-}(2,7\text{-}tBu_2\text{-}Flu)\}LnCH(SiMe_3)_2$ via a two-step, one-pot procedure involving salt metathesis between $YCl_3(THF)_n$ and $Li_2[Cp\text{-}CMe_2\text{-}(2,7\text{-}tBu_2\text{-}Flu)]$, followed by subsequent transmetallation with $LiCH(SiMe_3)_2$.[6] The title complex was characterised only by $^1H$ NMR and claimed to initiate living polymerization of MMA at 0° C. to give a polymer with weight average molecular weight distribution $M_w$ of 512,000, a polydispersity index D of 1.66 and 78% rr dyads. The polydispersity index D is defined by the ratio $M_w/M_n$ of the weight average molecular weight to the number average molecular weight.

There is therefore no unified method to prepare in good yield bridged metallocene components based on cyclopentadienyl-fluorenyl ligands and on Group III metals and to prepare therefrom catalyst systems having good polymerisation capability.

In addition all known metallocene catalyst systems based on metals Group IV of the Periodic Table require costly and dangerous activating agents and are not suitable to polymerise polar monomers.

It is an aim of the present invention to prepare in good yield bridged metallocene components based on cyclopentadienyl-fluorenyl ligands and based on Group III metals.

It is another aim of the present invention to prepare a catalyst component efficient in the controlled polymerisation of styrene.

It is a further aim of the present invention to prepare a catalyst component capable of polymerising syndiotactic methyl methacrylate.

More generally the present invention aims at preparing a catalyst system efficient in the controlled polymerisation of polar or non polar monomers.

Accordingly, the present invention discloses a metallocene catalyst component of the formula $$[(Flu\text{-}R''\text{-}Cp)_2M]^-[Li(ether)_4]^+ \qquad (I)$$

wherein Cp is a cyclopentadienyl, substituted or unsubstituted, Flu is a fluorenyl, substituted or unsubstituted, M is a metal Group III of the Periodic Table, and R'' is a structural bridge between Cp and Flu (9-position) imparting stereorigidity to the component.

The substituents on the cyclopentadienyl are not particularly limited, they can be the same or different and they include hydrocarbyls having from 1 to 20 carbon atoms.

The substituents on the fluorenyl are not particularly limited, they can be the same or different and they include hydrocarbyls having from 1 to 20 carbon atoms.

The type of bridge present between the cyclopentadienyl and the fluorenyl in the above-described catalysts is not itself particularly limited. Typically R'' comprises an alkylidene group having 1 to 20 carbon atoms, a germanium group (e.g. a dialkyl germanium group), a silicon group (e.g. a dialkyl silicon group), a siloxane group (e.g. a dialkyl siloxane group), an alkyl phosphine group or an amine group. Preferably, the substituent comprises a silyl radical or a hydrocarbyl radical having at least one carbon atom or one silica atom to form the bridge, such as a substituted or unsubstituted ethylenyl radical (e.g. —CH$_2$CH$_2$—). More preferably R" is isopropylidene (Me$_2$C), Ph$_2$C, ethylenyl, or Me$_2$Si, and most preferably R" is (Me$_2$C).

M is preferably yttrium, lanthanum or a member of the lanthanide series. Throughout this description, the term "lanthanide series" means the rare earth series of elements having atomic numbers of from 58 to 71. In the lanthanide series M is preferably neodymium, samarium. More preferably, M is yttrium.

The present invention also discloses a method for preparing the catalyst component (I) that comprises the steps of:
   a) suspending MCl$_3$(THF)$_n$ in ether;
   b) suspending a dilithium salt of (Cp-R"-Flu) in ether;
   c) carrying out the salt metathesis reaction of suspensions a) and b) at a temperature of from −80° C. to 60° C., and wherein the molar ratio of suspensions b) to a) is at least 2;
   d) crystallising the product obtained in c) from the ether;
   e) retrieving a crystalline powder of formula

[(Flu-R"-Cp)$_2$M]$^-$[Li(ether)$_4$]$^+$     (I)

The ether can be selected for example from tetrahydrofuran (THF), dioxane, diethyl oxide or diisopropyl oxide. Preferably, it is THF or diethyl oxide (Et$_2$O).

The temperature ranges preferably from −20° C. to 40° C., more preferably, it is room temperature (about 20° C.).

The crystalline powder obtained in step e) is extremely sensitive to air: it is not soluble in pentane, sparingly soluble in toluene and readily soluble in tetrahydrofuran (THF) or diethyl oxide.

The anion of ionic formula (I) is represented in FIG. 1.

The present invention also discloses the use of the catalyst component described hereabove, with or without an activating agent in the controlled polymerisation of polar or non polar monomers.

The present invention further discloses a process for homopolymerising polar or non polar monomers or for copolymerising polar or non polar monomers with a comonomer, said process comprising the steps of:
   providing the metallocene ionic component of formula (I);
   optionally providing an activating agent or a transfer agent;
   providing a monomer and an optional comonomer:
   maintaining the system under polymerising conditions;
   retrieving the desired polymer.

The optional activating agent includes Lewis acids having an ionising action and having a low or no coordinating capability. Typically, all the activators used with the metals Group IV of the Periodic Table can be used in the present invention. Suitable aluminium-containing activating agents comprise an alumoxane or an aluminium alkyl.

The alumoxanes that can be used in the present invention are well known and preferably comprise oligomeric linear and/or cyclic alkyl alumoxanes represented by the formula (II):

$$R\text{---}(\text{Al}\underset{|}{\text{---}}\text{O})_n\text{---}\text{AlR}_2 \qquad (II)$$
$$\phantom{R\text{---}(\text{Al}}R$$

for oligomeric linear alumoxanes; and formula (III)

$$\text{---}(\text{Al}\underset{|}{\text{---}}\text{O})_m\text{---} \qquad (III)$$
$$\phantom{\text{---}(\text{Al}}R$$

for oligomeric cyclic alumoxanes, wherein n is 1-40, preferably 10-20; m is 3-40, preferably 3-20; and R is a C$_1$-C$_8$ alkyl group, preferably methyl. Generally, in the preparation of alumoxanes from, for example, aluminium trimethyl and water, a mixture of linear and cyclic compounds is obtained.

Suitable boron-containing activating agents may comprise a triphenylcarbenium boronate, such as tetrakis-pentafluorophenyl-borato-triphenylcarbenium as described in EP-A-0427696:

$$\left[\underset{\text{Ph}}{\text{Ph}}\overset{\text{Ph}}{\underset{|}{\text{C}}}\right]^+ \quad \left[C_6F_5\text{---}\underset{\underset{C_6F_5}{|}}{\overset{C_6F_5}{\underset{|}{\text{B}}}}\text{---}C_6F_5\right]^-$$

or those of the general formula below, as described in EP-A-0277004 (page 6, line 30 to page 7, line 7):

$$[\text{L}'\text{-H}]^+ \quad \left[\text{Ar}_1\text{---}\underset{\underset{X_4}{|}}{\overset{\text{Ar}_2}{\underset{|}{\text{B}}}}\text{---}X_3\right]^-$$

Other preferred activating agents include hydroxy isobutylaluminium and a metal aluminoxinate.

Alkylating agents of the type MgR'$_2$ can also be used, wherein each R' is the same or different and is a hydrocarbyl having from 1 to 20 carbon atoms.

The transfer agents comprise for example H$_2$ and hydrosilanes of the formula HSiR'''$_3$ wherein each R''' is the same or different and is either an H atom or a hydrocarbyl having from 1 to 20 carbon atoms. It will be selected in accordance with the monomer to be polymerised.

The monomers that can be used in the present invention include non polar monomers such as for example ethylene, alpha-olefins, styrene and polar monomers such as for example acrylates or dienes. Preferably, styrene and methyl methacrylate have been used.

The catalyst system of the present invention may be employed in any type of homo- or co-polymerisation method, provided that the required catalytic activity is not impaired. In a preferred embodiment of the present invention, the catalyst system is employed in a bulk polymerisation process or in a solution polymerisation process, which is homogeneous, or in a slurry process, which is heterogeneous. In a solution process, typical solvents include THF or hydrocarbons having from 4 to 7 carbon atoms such as heptane, toluene or cyclohexane. In a slurry process, it is necessary to immobilise the catalyst on an inert support, particularly a porous solid support such as talc, inorganic oxides and resinous support materials such as polyolefin. Preferably, the support material is an inorganic oxide in its finely divided form.

Suitable inorganic oxide materials that are desirably employed in accordance with this invention include group IIA, IIIA, IVA, or IVB metal oxides such as silica, alumina and mixtures thereof. Other inorganic oxides that may be employed, either alone or in combination with the silica or alumina, are magnesia, titania, zirconia, and the like. Other suitable support materials, however, can be employed, for example, finely divided functionalised polyolefins such as finely divided polyethylene.

Preferably, the support is a silica support having a surface area of from 200-700 $m^2/g$ and a pore volume of from 0.5-3 ml/g.

The polymerisation temperatures range from 20° C. up to 100° C.

The present invention also covers the polymers obtainable by polymerisation in the presence of the catalysts components described hereabove.

LIST OF FIGURES

EXAMPLES

Figure 1:
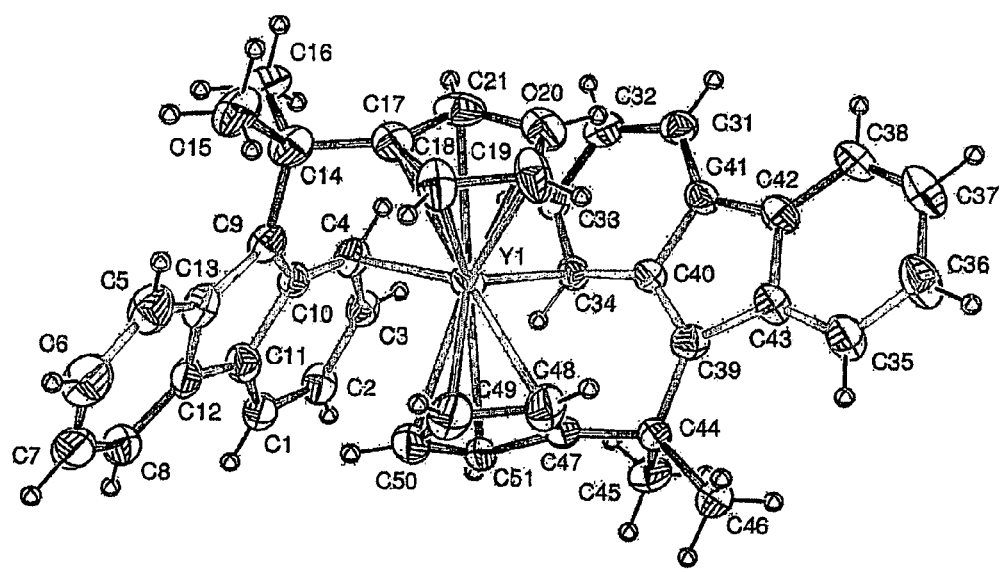
FIG. 1 represents the crystal structure of the anion of $[((\eta^3,\eta^5\text{-Flu-R''-Cp})(\eta^1,\eta^5\text{-Flu-CR-Cp})Y]^-[Li(ether)_4]^+$. Ellipsoids correspond to 50% probability.

Salt Metathesis Between [Flu-CMe$_2$-Cp]Li$_2$ and YCl$_3$(THF)$_n$ Using 2 Molar Equivalents of Ligand for One Molar Equivalent of Yttrium Salt. Synthesis of $[(Cp\text{-}CMe_2\text{-}Flu)_2Y]^-[Li(Et_2O)(THF)_3]^+$ To a solution of $C_{13}H_8H$—$CMe_2$-$C_5H_4H$ (0.2 g, 0.734 mmol) in diethyl ether (30 mL) at −10° C. was added under vigorous stirring 2 equiv. of n-BuLi (0.92 mL of a 1.6 M solution in hexane, 1.47 mmol). The reaction mixture was allowed to warm to room temperature. The solution turned dark-yellow and after 3 hours a yellow crystalline powder precipitated. To this suspension of the dilithium salt in ether cooled to −20° C. was added a suspension of YCl$_3$(THF)$_n$ (prepared from 0.072 g, 0.368 mmol of anhydrous YCl$_3$) in Et$_2$O (20 mL). Upon vigorous stirring and warming to ambient temperature the reaction mixture turned deep-red. The red solution was decanted from precipitate, concentrated in vacuo and cooled to −20° C. to yield 0.237 g of extremely air-sensitive deep-red crystals (70% yield).

The counteranion in $[(Cp\text{-}CMe_2\text{-}Flu)_2Y]^-[Li(Et_2O)(THF)_3]^+$ is represented by a lithium atom coordinated by four ether molecules, as observed in other ionic lanthanidocenes. The anion has an unprecedented structure with the yttrium atom coordinated by two non-equivalent (Flu-CMe$_2$-Cp) ligands. This represents the first structurally characterised example of an ionic group III metal compound with four Cp-type ligands. The bonding of the fluorenyl moieties was also unexpected. Scheme 1 below shows various bonding modes of fluorenyl ligands in ansa- and simple metallocenes of zirconium and lanthanides previously established by X-ray structures.

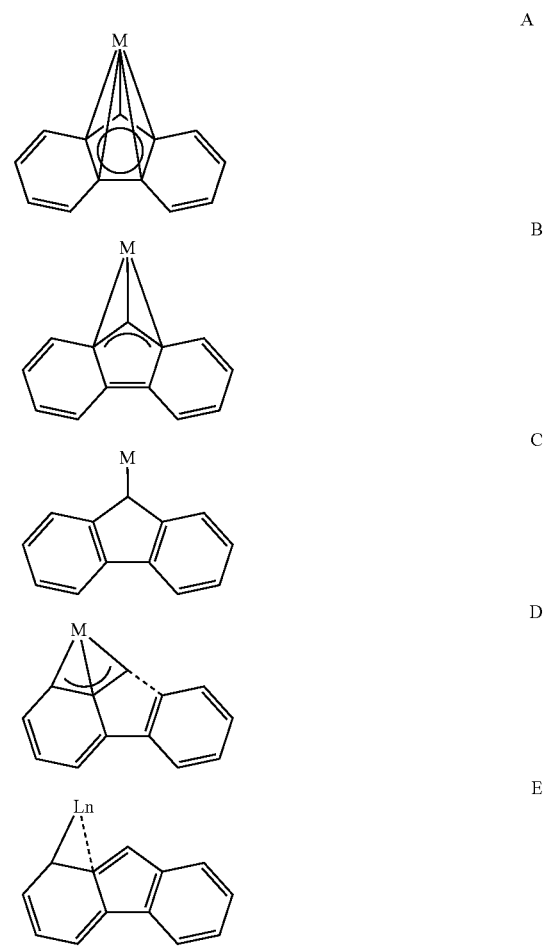

Scheme 1
Comparison of the bonding modes of the fluorenyl moieties observed in ansa-metallocenes (A-D) (M = Zr, Y, Sm) and in $[(\eta^3,\eta^5\text{-Flu-CMe}_2\text{-Cp})(\eta^1,\eta^5\text{-Flu-CMe}_2\text{-Cp})Y]^-[Li(Et_2O)(THF)_3]^+$ (D-E).

In most complexes, as observed for example by Lee et al. (Lee, M. H.; Hwang, J-W.; Kim, Y.; Kim, J.; Han, Y.; Do, Y., in Organometallics 1999, 18, 5124.) or by Evans et al. (Evans, W. J.; Gummersheimer, T. S.; Boyle, T. J.; Ziller, J. W., in Organometallics 1994, 13, 1281.), the metal is essentially symmetrically $\eta^5$-bonded to the five-membered ring of the fluorenyl ligand (A), as for example in ($\eta^5,\eta^5$-Cp-CMe$_2$-Flu)ZrCl$_2$ and ($\eta^5,\eta^5$-Cp-Me$_2$Si-Flu)YN(SiMe$_3$)$_2$, or $\eta^3$-bonded (B), as for example in ($\eta^5,\eta^3$-Flu)$_2$Sm(THF)$_2$ and ($\eta^5,\eta^3$-Cp-SiMe$_2$-Flu)YCl$_2$Li(OEt$_2$)$_2$. Very rarely, it is symmetrically $\eta^1$-bonded such as described in other compounds by Schmid and Vilnius (M. A. Schmid, H. G. Alt, W. Milius, J. Organomet. Chem., 1997, 541, 3.).

A rare non-symmetric $\eta^3$-allyl bonding mode (D) involving the bridgehead carbon atom of the central ring and the two adjacent carbon atoms of one six-membered ring was evidenced by Bochmann et al (Bochmann, M.; Lancaster, S. J.; Hursthouse, M. B.; Mazid, M. Organometallics 1993, 12, 4718.) in [($\eta^5,\eta^3$-Cp-CMe$_2$-Flu)Zr(μ-H)(Cl)]$_2$, with Zr—C bond distances in the range 2.608(3)-2.686(3) Å. This last bonding mode is found in one of the two fluorenyl moieties, with the bond length ranges as follows:

Y—C(4) in the range of 2.690-2.789 Angströms,
Y—C(10) in the range of 2.749-2.806 Angströms,
Y—C(9) in the range of 2.894-3.065 Angströms.

The second fluorenyl moiety differs from the first fluorenyl moiety. The yttrium-carbon bond distances are as follows:

Y—C(34) in the range of 2.671-2.722 Angströms,
Y—C(40) in the range of 3.101-3.177 Angströms, and
Y—C(39) in the range of 3.540-3.633 Angströms.

The two last bond distances appear beyond significant bonding interaction, which is supported by Extended Huckle Molecular Orbitals (EHMO) method and Density Functional Theory (DFT) computations. The other fluorenyl moiety is thus coordinated via a new bonding mode involving only one carbon atom of the phenyl ring (E).

Considering that the two Cp rings are $\eta^5$-coordinated, compound $[(\eta^3,\eta^5$-Flu-CMe$_2$-Cp)($\eta^1,\eta^5$-Flu-CMe$_2$-Cp)Y]$^-$[Li(Et$_2$O)(THF)$_3$]$^+$, is thus best formally described as an 18-electron complex.

Polymerization of Methyl Methacrylate (MMA)

To a preweighted amount of about 10 mg of is [(Cp-CMe$_2$-Flu)$_2$Y]$^-$[Li(Et$_2$O)(THF)$_3$]$^+$, methyl methacrylate (3.0 mL, 27.7 mmol) was added by syringe and vigorous stirring at the appropriate temperature was immediately started. After a given time period, the Schlenk tube was opened to air and acetone (30 mL) was added to quench the reaction and dissolve the polymer formed. The polymer was precipitated by adding methanol (ca. 200 mL), filtered, washed twice with methanol (30 mL) and dried in vacuo. The number average molecular weight Mn and the weight average molecular weight Mw were determined by GPC in THF using universal calibration relative to polystyrene standards. The molecular weight distribution is described by the polydispersity index D defined as the ratio Mn/Mw of the weight average molecular weight to the number average molecular weight. The polymer microstructure was determined by $^1$H NMR in CDCl$_3$.

The polymerisation experiment was repeated under different polymerisation conditions as disclosed in Table I.

TABLE I

| Polym. Condit | T (° C.) | time (h) | Yield (%) | $M_n$ (10$^3$) | $M_w/M_n$ | Tacticity rr | mr | mm |
|---|---|---|---|---|---|---|---|---|
| Bulk | 20 | 25 | 5 | 209 | 1.76 | 67 | 29 | 3 |
| " | 50 | 12 | 43 | 346 | 1.49 | 64 | 32 | 4 |

The ratio [MMA]/[Ln] was of about 300.

Figure 2:
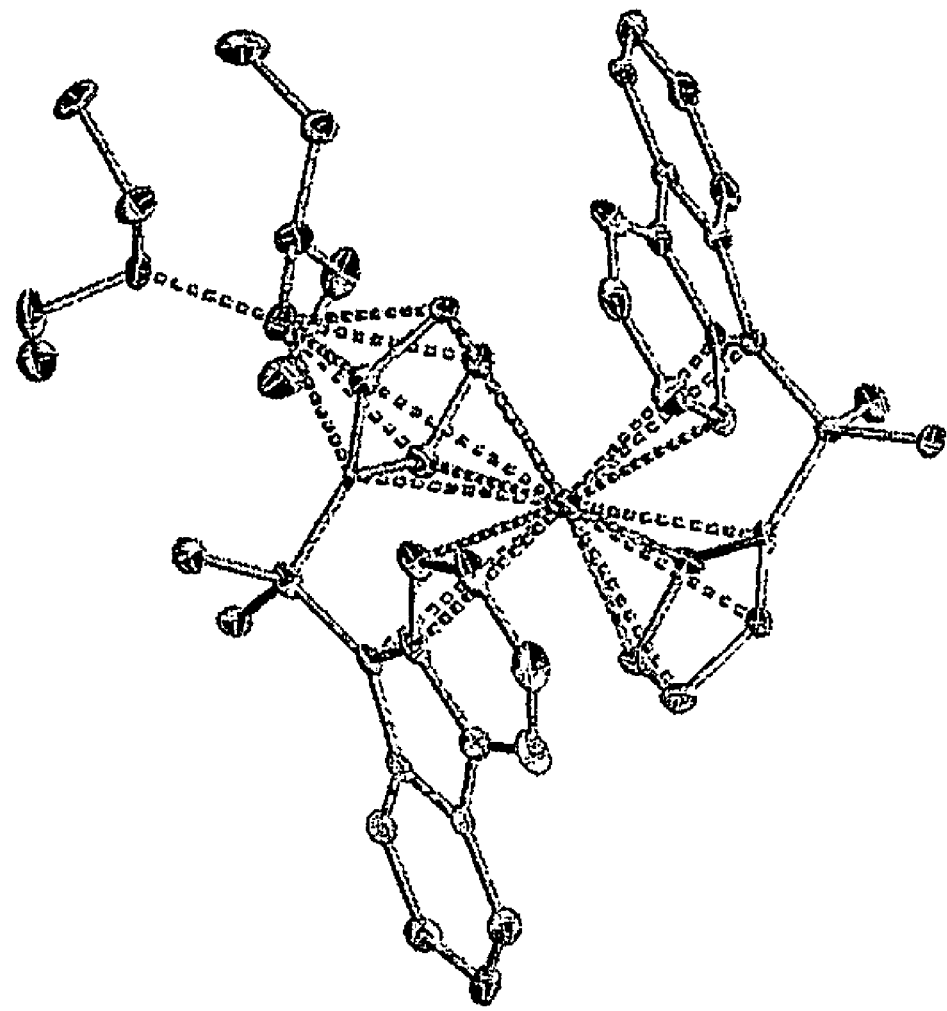
FIG. 2 represents the crystal structure of the anion of $[(\eta^3,\eta^5\text{-Flu-R''-Cp})(\eta^1,\eta^5\text{-Flu-CR-Cp})La]^-[Li(ether)_4]^+$

Similar synthesis experiments were carried out using LaCl$_3$ THF adduct. They led to the isolation of compound [(Cp-CMe$_2$-Flu)$_2$La]$^-$[Li(Et$_2$O)(THF)$_3$]$^+$ showing an anionic lanthanum-centred core with two bonded Cp-Flu moieties (see FIG. 2). In this structure, however, the lithium cation is not independent and is bridged to one cyclopentadienyl ring.

Polymerization of Styrene

To a preweighted amount of lanthanide compound (ca. 10 mg), styrene (3.0 mL, 25.96 mmol) was added by syringe and vigorous stirring at the appropriate temperature was immediately started. After a given time period, the Schlenk tube was opened to air and 10% solution of HCl acid in the methanol (1 mL) was added to quench the reaction. The polymer was precipitated by adding methanol (ca. 200 mL), filtered, washed twice with methanol (30 mL) and dried in vacuo. Results are displayed in Table II.

TABLE II

| Polym. Cond. | Temp. (° C.) | Time (h) | Yield (%) | Mn (10$^3$) | Mw/Mn |
|---|---|---|---|---|---|
| Bulk | 20 | 48 | 4 | 151 | 1.85 |
| Bulk | 50 | 48 | 12 | 211 | 1.90 |

The invention claimed is:

1. A metallocene catalyst component characterized by the formula:

wherein Cp is a substituted or unsubstituted cyclopentadienyl group, Flu is a substituted or unsubstituted fluorenyl, M is a metal Group III of the Periodic Table, and R" is a structural bridge between Cp and Flu imparting stereorigidity to the component.

2. The metallocene catalyst component of claim 1 wherein M is yttrium, lanthanum, neodymium or samarium.

3. The metallocene catalyst component of claim 1 wherein M is yttrium.

4. The metallocene catalyst component of claim 3 wherein R" an isopropylidene group, a diphenylmethylene group, an ethylenyl group or a dimethylsilyl group.

5. The metallocene catalyst component of claim 4 wherein R" is an isopropylidene group.

6. The metallocene catalyst component of claim 3 wherein said ether group is selected from the group consisting of tetrahydrofuran, dioxane, diethyl oxide and diisopropyl oxide.

7. The metallocene catalyst component of claim 6 wherein said ether group is tetrahydrofuran or diethyl oxide.

8. In the preparation of a metallocene catalyst component characterized by the formula:

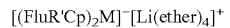

wherein Cp is a substituted or unsubstituted cyclopentadienyl group, Flu is a substituted or unsubstituted fluorenyl group, R" is a structural bridge between Cp and Flu imparting stereorigidity to the component and M is a metal from Group III of the Periodic Table, the process comprising:

(a) providing a suspension of MCl3(THF)n in an ether;
(b) providing a suspension of a dilithium salt of (CpR"Flu) in an ether;
(c) reacting suspensions (a) and (b) at molar ratio of suspension (b) to suspension (a) of at least 2 in a salt metathesis reaction at a temperature of from –80° C. to 60° C.; and
(d) crystallizing the product of said salt metathesis reaction from said ether to recover said metallocene catalyst component in the form of a crystalline powder.

9. The method of claim 8 wherein said salt metathesis reaction is carried out at a temperature of about 20° C.

10. The method of claim 8 wherein the ether is tetrahydrofuran or diethyl oxide.

11. A polymerization process comprising:

(a) providing a catalyst system effective for the polymerization of ethylenically unsaturated monomers, which catalyst system comprises a metallocene catalyst component characterized by the formula:

wherein Cp is a substituted or unsubstituted cyclopentadienyl group, Flu is a substituted or unsubstituted fluorenyl group, R" is a structural bridge between Cp and Flu imparting stereorigidity to the component and M is a metal Group III of the Periodic Table;

(b) contacting said catalyst system with an ethylenically unsaturated monomer in a polymerization reaction zone under polymerization conditions to form a polymer product; and (c) recovering said polymer product from said polymerization reaction zone.

12. The process of claim 11 wherein said monomer is a non-polar monomer selected from the group consisting of ethylene, $C_{3+}$ alpha olefins, and styrene.

13. The process of claim 11 wherein said monomer is a polar monomer selected from the group consisting of methacrylate and a diene.

14. The process of claim 11 wherein in said metallocene catalyst component M is yttrium, lanthanum, neodymium or samarium and R" an isopropylidene group, a diphenylmethylene group, an ethylenyl group or a dimethylsilyl group.

15. The process of claim 14 wherein in said metallocene catalyst component said ether group is selected from the group consisting of tetrahydroftiran dioxane, diethyl oxide and diisopropyl oxide.

* * * * *